United States Patent
Candau et al.

(10) Patent No.: US 6,419,908 B1
(45) Date of Patent: Jul. 16, 2002

(54) UV-PHOTOSTABILIZATION OF DIBENZOYLMETHANE SUNSCREENS BY COMPOUNDING WITH MICRONIZED INSOLUBLE SCREENING AGENTS

(75) Inventors: Didier Candau, Bievres; Anne-Marie Pisson, Boussy St Antoine, both of (FR)

(73) Assignee: Societe L'Oreal, Paris (FR)

( * ) Notice: Subject to any disclaimer, the term of this patent is extended or adjusted under 35 U.S.C. 154(b) by 0 days.

(21) Appl. No.: 09/693,887

(22) Filed: Oct. 23, 2000

(30) Foreign Application Priority Data

Oct. 22, 1999 (FR) .............................. 99/13222

(51) Int. Cl.[7] .............................. A61L 7/42; A61L 7/44; A61L 7/00
(52) U.S. Cl. ........................ 424/59; 424/60; 424/400; 424/401
(58) Field of Search .......................... 424/59, 60, 400, 424/401

(56) References Cited

U.S. PATENT DOCUMENTS

| 5,733,532 A | 3/1998 | Raspanti et al. ............... 424/59 |
| 5,882,633 A | 3/1999 | Pisson et al. ................. 424/59 |
| 5,985,925 A | 11/1999 | Josso et al. ................... 424/59 |

FOREIGN PATENT DOCUMENTS

| EP | 0 824 909 A2 | 2/1998 |
| EP | 0 848 946 A1 | 6/1998 |
| EP | 0 893 119 A2 | 1/1999 |

*Primary Examiner*—Shelley A. Dodson
(74) *Attorney, Agent, or Firm*—Burns, Doane, Swecker & Mathis, L.L.P.

(57) ABSTRACT

The UV-stability of the UV-photoprotecting dibenzoylmethane compounds is conspicuously enhanced, as is the UV-stability of cosmetic/dermatological sunscreen compositions comprised thereof, by formulating such dibenzoylmethane compounds with an effective UV-photostabilizing amount of at least one micronized insoluble organic UV-screening agent, the mean particle size of said micronized particles ranging from 0.01 to 2 μm.

31 Claims, No Drawings

UV-PHOTOSTABILIZATION OF DIBENZOYLMETHANE SUNSCREENS BY COMPOUNDING WITH MICRONIZED INSOLUBLE SCREENING AGENTS

CROSS-REFERENCE TO COMPANION APPLICATIONS

Copending applications Ser. No. 09/693,888, Ser. No 09/693,889 and Ser. No. 09/693,894, each assigned to the assignee hereof, each filed concurrently herewith and each also hereby expressly incorporated by reference.

CROSS-REFERENCE TO PRIORITY APPLICATION

This application claims priority under 35 U.S.C. §119 of FR-99/13222, filed Oct. 22, 1999, hereby expressly incorporated by reference.

BACKGROUND OF THE INVENTION

1. Technical Field of the Invention

The present invention relates to improving the stability of at least one UV-photoprotecting dibenzoylmethane compound with respect to UV-radiation, by formulating such dibenzoylmethane compound with an effective UV-photostabilizing amount of at least one insoluble organic UV-screening agent in the micronized form or state, the mean size of the particles of which ranging from 0.01 to 2 $\mu$m.

The present invention also relates to formulating an insoluble organic UV-screening agent in the micronized form, the mean size of the particles of which ranging from 0.01 to 2 $\mu$m, into cosmetic/dermatological compositions comprising at least one UV-photoprotecting dibenzoylmethane compound, wherein the photostability of said at least one dibenzoylmethane compound with respect to UV radiation is conspicuously enhanced.

2. Description of the Prior Art

It is known to this art that light radiation of wavelengths of from 280 nm to 400 nm permits tanning of the human epidermis, and that radiation of wavelengths more particularly of from 280 nm to 320 nm, i.e., UV-B radiation, causes erythemas and skin burns which can hinder the development of natural tanning.

For these reasons as well as for aesthetic reasons, there is a constant demand to control this natural tanning such as to thereby control the color of the skin; it is therefore advisable to screen out UV-B radiation.

It is also known to this art that UV-A radiation of wavelengths of from 320 nm to 400 nm, which promotes tanning of the skin, also is capable of causing damage thereto, in particular in the case of a sensitive skin or of a skin continually exposed to solar radiation. UV-A radiation causes, in particular, loss of elasticity of the skin and the appearance of wrinkles which promotes premature skin aging. UV-A radiation promotes the onset of the erythema reaction or amplifies this reaction in certain individuals and may even be responsible for phototoxic or photoallergic reactions. Thus, for aesthetic and cosmetic reasons such as the preservation of the natural elasticity of the skin for example, an increasing number of individuals seek to control the effect of UV-A radiation on their skin. It is therefore desirable to also screen out UV-A radiation.

In this respect, a particularly advantageous class of UV-A screening agents is that of the dibenzoylmethane compounds, and in particular 4-(tert-butyl)-4'-methoxydibenzoylmethane; this is because these derivatives or compounds exhibit a high intrinsic absorption power. Such dibenzoylmethane compounds, which are now well known per se as screening agents active in the UV-A range, are described, in particular, in FR-A-2,326,405 and FR-A-2,440,933 and in EP-A-0,114,607. Too, 4-(tert-butyl)-4'-methoxydibenzoylmethane is currently commercially available under the trademark "Parsol 1789" by Hoffmann Laroche.

Unfortunately, the dibenzoylmethane derivatives are compounds which are relatively sensitive to ultraviolet radiation (in particular UV-A radiation), namely, more specifically, they have an unfortunate tendency to decompose more or less rapidly under the effect or influence of UV-A radiation. Thus, this substantial lack of photochemical stability of dibenzoylmethane compounds under the influence of ultraviolet radiation, to which they are naturally intended to be subjected or exposed, does not permit a guarantee of constant protection during prolonged exposure to the sun, such that repeated applications at regular and frequent intervals of time are necessary in order to provide the user with effective protection of the skin against UV rays.

Thus, serious need continues to exist for the effective photostabilization of dibenzoylmethane compounds with respect to UV radiation.

SUMMARY OF THE INVENTION

It has now surprisingly and unexpectedly been determined that compounding/formulating the above-mentioned dibenzoylmethane compounds with an effective UV-stabilizing amount of an insoluble organic UV-screening agent in the micronized form, substantially and notably enhanced the photochemical stability (or photostability) of such dibenzoylmethane derivatives.

Briefly, the present invention features the stabilization of dibenzoylmethane compounds with respect of UV radiation (wavelengths ranging from 280 nm to 400 nm, approximately), in particular solar radiation, by formulating said dibenzoylmethane compounds with an effective UV-photostabilizing amount of at least one insoluble organic UV screening agent in the micronized form.

DETAILED DESCRIPTION OF BEST MODE AND SPECIFIC/PREFERRED EMBODIMENTS OF THE INVENTION

More particularly, according to the present invention, by the term "insoluble organic UV-screening agent" are intended organic UV-screening agents having a solubility in water at 25° C. of less than 0.1% by weight and a solubility in liquid paraffin at 25° C. of less than 1% by weight.

By the term "effective UV-photostabilizing amount of insoluble organic UV-screening agent" is intended an amount sufficient to provide a notable and significant improvement in the UV-photostability of the dibenzoylmethane compound(s) comprising UV-photoprotective cosmetic compositions. This minimum amount of UV-photostabilizing agent to be formulated, which can vary depending on the nature of the cosmetically acceptable vehicle, diluent or carrier included in the composition, can be determined without any difficulty via a conventional test for the measurement of photostability, such as that given in the examples below.

This invention thus also features formulating an insoluble organic UV-screening agent into a cosmetic/dermatological composition comprising at least one dibenzoylmethane compound for the purpose of improving the stability with respect to UV-radiation of any such dibenzoylmethane compound present.

The insoluble organic screening agents according to the invention are provided in micronized form. The mean or average size of the particles ranges from 0.01 µm to 2 µm and more preferably from 0.02 µm to 1.5 µm and even more preferably from 0.03 µm to 1.0 µm.

The insoluble organic screening agents according to the invention may be provided in the desired particulate form by any appropriate means such as, in particular, grinding in the dry state or in solvent medium, sieving, spray-drying, micronization or spraying.

The insoluble organic screening agents according to the invention in micronized form may, in particular, be provided by a method of grinding an insoluble UV-screening agent in the form of particles having a coarse size in the presence of an appropriate surfactant which makes it possible to enhance the dispersion of the particles thus obtained in the cosmetic formulations.

One embodiment of a method of micronization of insoluble organic screening agents is described in GB-A-2, 303,549 and EP-A-893119 incorporated by reference herein. The grinding apparatus according to the invention may be a jet mill, a ball mill, a vibratory mill or a hammer mill and preferably a mill featuring high-speed agitation or an impact mill and more particularly a rotating ball mill, a vibratory mill, a tube mill or a rod mill.

According to this particular methodology, the alkyl polyglucosides having the structure $C_nH_{2n-1}O(C_6H_{10}O_5)_xH$ in which n is an integer from 8 to 16 and x is the average degree of polymerization of the structural unit $(C_6H_{10}O_5)$ and ranges from 1.4 to 1.6, are included as surfactants for the grinding of the screening agents. They are advantageously selected from among $C_1$–$C_{12}$ esters of a compound having the structure $C_nH_{2n+1}O(C_6H_{10}O_5)_xH$ and more precisely an ester prepared by reacting a $C_1$–$C_{12}$ carboxylic acid such as formic, acetic, propionic, butyric, sulfosuccinic, citric or tartaric acid with one or more free OH functions on the glucoside unit $(C_6H_{10}O_5)$. Such surfactants are typically employed at a concentration ranging from 1% to 50% by weight and more preferably from 5% to 40% by weight relative to the insoluble screening agent in its micronized form.

As indicated above, the dibenzoylmethane compounds sought to be photostabilized according to the present invention are already well known per se and described, in particular, in FR-A-2,326,405, FR-A-2,440,933 and EP-A-0,114,607 (hereby expressly incorporated by reference).

Consistent herewith, it is envisaged, of course, to employ one or more dibenzoylmethane compounds.

Particularly exemplary dibenzoylmethane derivatives according to the present invention include:
2-Methyldibenzoylmethane,
4-Methyldibenzoylmethane,
4-Isopropyldibenzoylmethane,
4-Tert-butyldibenzoylmethane,
2,4-Dimethyldibenzoylmethane,
2,5-Dimethyldibenzoylmethane,
4,4'-Diisopropyldibenzoylmethane,
4,4'-Dimethyldibenzoylmethane,
4-Tert-butyl-4'-methoxydibenzoylmethane,
2-Methyl-5-isopropyl-4'-methoxydibenzoylmethane,
2-Methyl-5-tert-butyl-4'-methoxydibenzoylmethane,
2,4-Dimethyl-4'-methoxydibenzoylmethane,
2,6-Dimethyl-4-tert-butyl-4'-methoxydibenzoylmethane.

Very particularly preferred according to the present invention is 4-(tert-butyl)-4'-methoxydibenzoylmethane, in particular that commercially available under the trademark "Parsol 1789" by Givaudan. This UV-screening agent has the following structural formula:

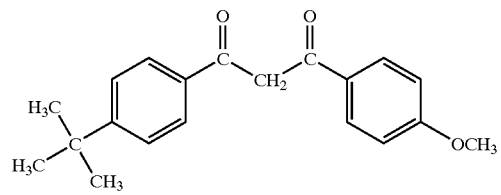

Another dibenzoylmethane compound which is preferred according to this invention is 4-isopropyldibenzoylmethane, a UV-screening agent marketed under the trademark "Eusolex 8020" by Merck. It has the following structural formula:

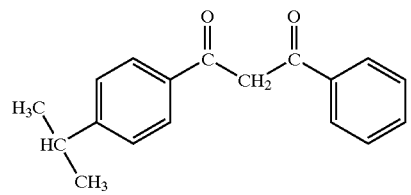

The dibenzoylmethane derivative or derivatives can be present in the compositions in accordance with the invention, or in the compositions intended to be stabilized in accordance herewith, at concentrations ranging from 0.01% to 10% by weight and preferably ranging from 0.1% to 6% by weight with respect to the total weight of the composition.

The insoluble organic UV-screening agents in accordance with this invention may be selected, in particular, from among the organic UV-screening agents of the oxanilide type, of the triazine type, of the triazole type, of the vinylamide type and of the cinnamide type.

Exemplary UV-screening agents of the oxanilide type include those having the structural formula (1):

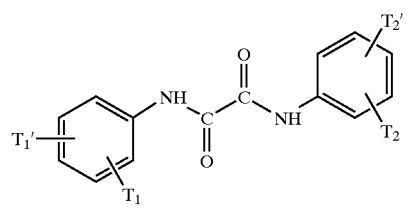

in which $T_1$, $T'_1$, $T_2$ and $T'_2$, which may be identical or different, are each a $C_1$–$C_8$ alkyl radical or a $C_1$–$C_8$ alkoxy radical. These compounds are described in WO-95/22,959.

Exemplary thereof are the commercial products TINUVIN 315 and TINUVIN 312 marketed by Ciba-Geigy and respectively having the structural formulae:

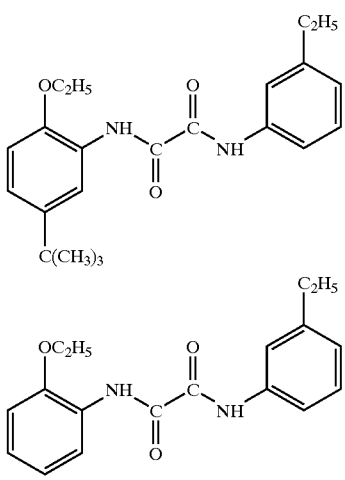

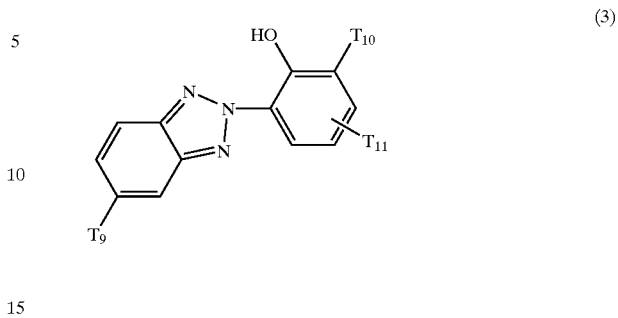

following structural formula (3) as described in WO-95/22,959 (also expressly incorporated by reference):

in which $T_9$ is a hydrogen atom or a $C_1$–$C_{18}$ alkyl radical; and $T_{10}$ and $T_{11}$, which may be identical or different, are each a $C_1$–$C_{18}$ alkyl radical which is optionally substituted with a phenyl radical.

Also exemplary insoluble UV-screening agents of the triazine type in accordance with the invention are the insoluble derivatives of s-triazine substituted by benzalmalonate and/or phenylcyanoacrylate groups, such as those described in EP-A-0,790,243 (also expressly incorporated by reference).

Among these UV-screening agents of the triazine type, the following compounds are more particularly exemplary:

2,4,6-tris(diethyl 4'-aminobenzalmalonate)-s-triazine;
2,4,6-tris(diisopropyl 4'-aminobenzalmalonate)-s-triazine;
2,4,6-tris(dimethyl 4'-aminobenzalmalonate)-s-triazine;
2,4,6-tris(ethyl α-cyano-4-aminocinnamate)-s-triazine.

Among the insoluble UV-screening agents of the triazine type in accordance with the invention are those having the following structural formula (2):

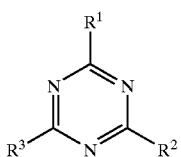

in which $R^1$, $R^2$, $R^3$ are independently phenyl, phenoxy, pyrrolo, in which the phenyl, phenoxy and pyrrolo radicals are optionally substituted with one, two or three substituents selected from among OH, $C_1$–$C_{18}$ alkyl or alkoxy, $C_1$–$C_{18}$ carboxyalkyl, $C_5$–$C_8$ cycloalkyl, a methylidenecamphor group, a group —(CH=CH)$_n$(CO)—OR$^4$, wherein $R^4$ is either $C_1$–$C_{18}$ alkyl or cinnamyl, and n is equal to 0 or 1.

These compounds are described in WO-97/03,642, GB-2,286,774, EP-0-743,309, WO-98/22,447, GB-2,319,523 (expressly incorporated by reference).

Among the insoluble UV-screening agents of the triazine type in accordance with the invention, exemplary are the insoluble derivatives of s-triazine substituted by benzotriazole and/or benzothiazole groups, such as those described in WO-98/25,922 (also expressly incorporated by reference).

More particularly exemplary are:

2,4,6-tris[(3'-benzotriazol-2-yl-2'-hydroxy-5'-methyl)phenylamino]-s-triazine; and
2,4,6-tris[(3'-benzotriazol-2-yl-2'-hydroxy-5'-ter-octyl)phenylamino]-s-triazine.

Exemplary organic UV-screening agents of the triazole type in accordance with the invention are those of the following structural formula (3) as described in WO-95/22,959 (also expressly incorporated by reference):

Exemplary compounds of formula (7) are the commercial products TINUVIN 328, 320, 234 and 350 marketed by Ciba-Geigy having the following structural formulae:

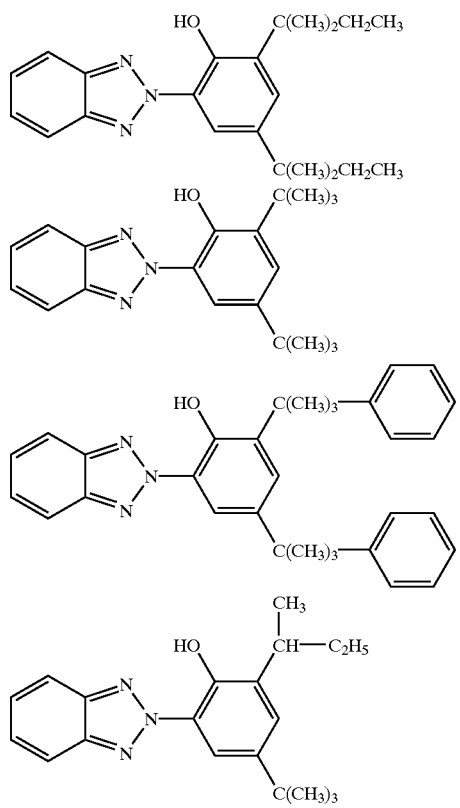

Exemplary organic UV-screening agents of the triazole type in accordance with the invention are the compounds described in U.S. Pat. Nos. 5,687,521, 5,687,521, 5,373,037, 5,362,881 and, in particular, [2,4'-dihydroxy-3-(2H-benzotriazol-2-yl)-5-(1,1,3,3-tetramethylbutyl)-2'-n-octoxy-5'-benzoyl]diphenylmethane marketed under the trademark MIXXIM PB30 by Fairmount Chemical and having the structural formula:

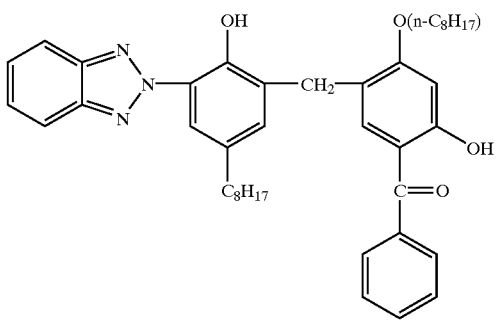

And exemplary organic UV-screening agents of the benzotriazole type in accordance with the invention are the methylenebis(hydroxyphenyl-benzotriazole) compounds having the following structural formula:

(4)

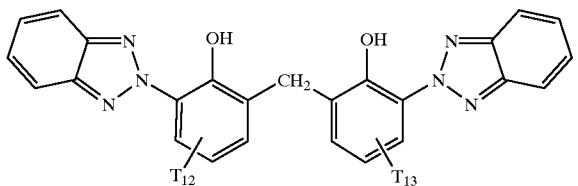

in which the radicals $T_{12}$ and $T_{13}$, which may be identical or different, are each a $C_1$–$C_{18}$ alkyl radical which may be substituted with one or more radicals selected from among a $C_1$–$C_4$ alkyl, a $C_5$–$C_{12}$ cycloalkyl, or an aryl radical. These compounds are per se known and are described in U.S. Pat. Nos. 5,237,071 and 5,166,355, GB-A-2,303,549, DE-197, 26,184 and EP-A-893,119 (also expressly incorporated by reference).

In formula (4) above, the $C_1$–$C_{18}$ alkyl radicals may be linear or branched and include, for example, methyl, ethyl, n-propyl, isopropyl, n-butyl, isobutyl, tert-butyl, tert-octyl, n-amyl, n-hexyl, n-heptyl, n-octyl, iso-octyl, n-nonyl, n-decyl, n-undecyl, n-dodecyl, tetradecyl, hexyldecyl or octadecyl; the $C_5$–$C_{12}$ cycloalkyl radicals include, for example, cyclopentyl, cyclohexyl, cyclooctyl; and the aryl radicals include, for example, phenyl or benzyl.

Among the compounds of formula (4), those having the following structural formula are particularly preferred:

compound (a)

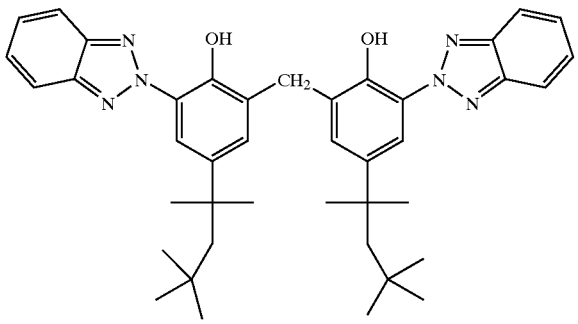

compound (b)

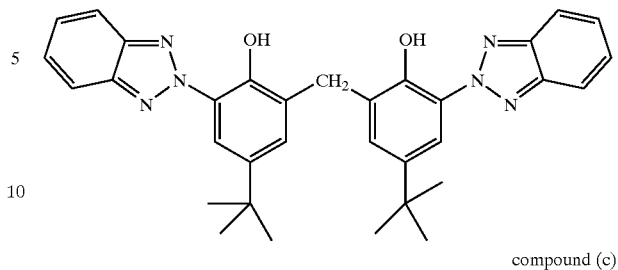

compound (c)

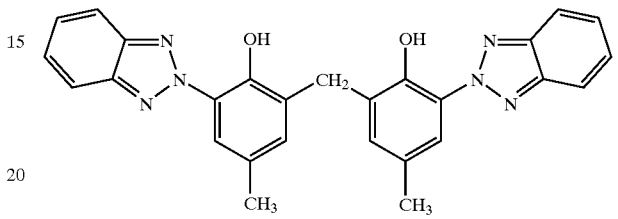

The compound (a) with the nomenclature 2,2'-methylenebis[6-(2H-benzotriazol-2-yl)-4-(1,1,3,3-tetramethylbutyl)phenol] is marketed under the trademark MIXXIM BB/100 by Fairmount Chemical. It is marketed in micronized form under the trademark TINOSORB M by Ciba-Geigy.

The compound (c) with the nomenclature 2,2'-methylenebis[6-(2H-benzotriazol-2-yl)-4-(methyl)phenol] is marketed under the trademark MIXXIM BB/200 by Fairmount Chemical.

Among the organic screening agents of the vinylamide type in accordance with the invention, exemplary are the compounds of the following formulae which are described in WO-95/22,959 (expressly incorporated by reference):

$$T_{14}\text{—}(Y)r\text{-}C(=O)\text{—}C(T_{15})=C(T_{16})\text{—}N(T_{17})(T_{18}) \quad (5)$$

in which $T_{14}$ is a $C_1$–$C_{18}$, preferably $C_1$–$C_5$, alkyl radical or a phenyl group which is optionally substituted with one, two or three radicals selected from among OH, $C_1$–$C_{18}$ alkyl, $C_1$–$C_8$ alkoxy, or a radical —C(=O)—O$T_{19}$ wherein $T_{19}$ is a $C_1$–$C_{18}$ alkyl radical; $T_{15}$, $T_{16}$, $T_{17}$ and $T_{18}$, which may be identical or different, are each a $C_1$–$C_{18}$, preferably $C_1$–$C_5$, alkyl radical or a hydrogen atom; Y is N or O and r is equal to 0 or 1.

Among these compounds, particularly representative are:

4-octylamino-3-penten-2-one;

ethyl 3-octylamino-2-butenoate;

3-octylamino-1-phenyl-2-buten-1-one;

3-dodecylamino-1-phenyl-2-buten-1-one.

Exemplary insoluble organic screening agents of the cinnamamide type are those compounds described in WO-95/22,959 (expressly incorporated by reference) and having the following structural formula:

(6)

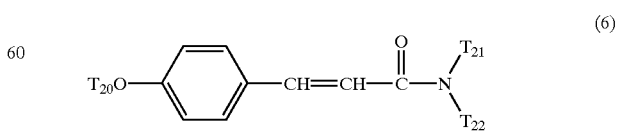

in which $T_{20}$ is a hydroxyl or $C_1$–$C_4$ alkoxy, preferably methoxy or ethoxy, radical; $T_{21}$ is hydrogen, $C_1$–$C_4$ alkyl, preferably methyl or ethyl; $T_{22}$ is a radical —(CONH)s- phenyl wherein s is equal to 0 or 1 and the phenyl group may be substituted with one, two or three groups selected from among OH, $C_1$–$C_{18}$ alkyl, $C_1$–$C_8$ alkoxy, or a radical —C(=O)—$OT_{23}$ wherein $T_{23}$ is a $C_1$–$C_{18}$ alkyl and more preferably $T_{23}$ is a phenyl, 4-methoxyphenyl or phenylaminocarbonyl group.

Also exemplary are the cinnamamide dimers such as those described in U.S. Pat. No. 5,888,481, for example, the compound having the structural formula:

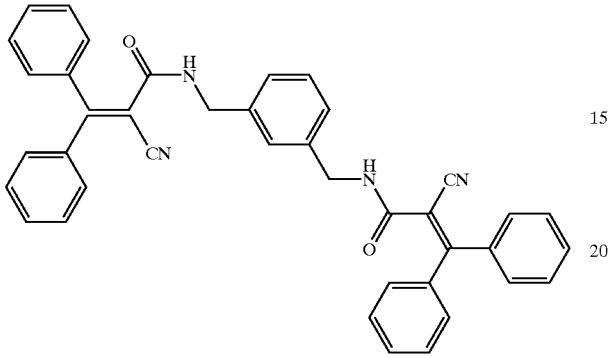

Another specific family of insoluble organic UV-screening agents in accordance with the invention are the polyvalent metal salts (for example $Ca^{2+}$, $Zn^{2+}$, $Mg^{2+}$, $Ba^{2+}$, $Al^{3+}$ or $Zr^{4+}$) of sulfonic or carboxylic organic screening agents such as the polyvalent metal salts of sulfonated derivatives of benzylidenecamphor, for example those described in FR-A-2,639,347; the polyvalent metal salts of sulfonated derivatives of benzimidazole, for example those described in EP-A-893,119; and the polyvalent metal salts of cinnamic acid derivatives, for example those described in JP-87/166,517.

Also representative are the metal or ammonium or substituted ammonium complexes of organic UV-A and/or UV-B screening agents as described in WO-93/10,753, WO-93/11,095 and WO-95/05,150.

The micronized insoluble organic screening agent(s) according to the invention are generally present in the screening compositions according to the invention at a total concentration ranging from 0.1% and 15% by weight approximately, and preferably from 0.2% and 10% by weight approximately, relative to the total weight of the composition.

This invention also features cosmetic or dermatological compositions comprising at least one emulsion of the subject compounds.

The anti-sun cosmetic compositions according to the invention may of course contain one or more additional organic screening agents which are active in UV-A and/or UV-B ranges (absorbers), which are soluble in at least one of the phases of the subject compositions. These additional screening agents may be selected, in particular, from among the cinnamic derivatives; the dibenzoylmethane derivatives; the salicylic derivatives, the camphor derivatives; the triazine derivatives such as those described in U.S. Pat. No. 4,367,390, EP-0,863,145, EP-0,517,104, EP-0,570,838, EP-0,796,851, EP-0,775,698, EP-0,878,469 and EP-0,933,376; the benzophenone derivatives; the dimers derived from α-alkylstyrene such as those described in DE-198,55,649; the β,β'-diphenylacrylate derivatives; the benzimidazole derivatives; the bisbenzoazolyl derivatives as described in EP-A-0,669,323 and U.S. Pat. No. 2,463,264; the p-aminobenzoic acid derivatives; the polymer screening agents and silicone screening agents such as those described, in particular, in WO-93/04,665.

Exemplary such additional sunscreening agents active in the UV-A and/or UV-B ranges, which are soluble in at least one of the phases of the subject compositions, include:

p-aminobenzoic acid;
oxyethylenated p-aminobenzoate (25 mol);
2-ethylhexyl p-dimethylaminobenzoate;
N-oxypropylenated ethyl p-aminobenzoate;
glyceryl p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyl-dibenzoylmethane;
2-ethylhexyl 4-methoxycinnamate;
methyl diisopropylcinnamate;
isoamyl 4-methoxycinnamate;
diethanolamine 4-methoxycinnamate;
menthyl anthranilate;
2-ethylhexyl-2-cyano-3,3'-diphenylacrylate;
ethyl 2-cyano-3,3'-diphenylacrylate;
2-phenylbenzimidazole-5-sulfonic acid and salts thereof;
3-(4'-trimethylammonium)benzylidenebornan-2-one methyl sulfate;
2-hydroxy-4-methoxybenzophenone;
2-hydroxy-4-methoxybenzophenone-5-sulfonate;
2,4-dihydroxybenzophenone;
2,2'-4,4'-tetrahydroxybenzophenone;
2,2'-dihydroxy-4,4'-dimethoxybenzophenone;
2-hydroxy-4-n-octoxybenzophenone;
2-hydroxy-4-methoxy-4'-methylbenzophenone;
a-(2-oxoborn-3-ylidene)tolyl-4-sulfonic acid and its soluble salts;
3-(4'-sulfo)benzylidenebornan-2-one and its soluble salts;
3-(4'-methylbenzylidene)-d,1-camphor;
3-benzylidene-d,1-camphor;
1,4-benzene[di(3-methylidene-10-camphorsulfonic)] acid and its soluble salts;
urocanic acid;
2,4-bis{[4-2-ethylhexyloxy)]-2-hydroxy]phenyl}-6-(4-methoxyphenyl)-1,3,5-triazine;
the polymer of N-(2 and 4)-[(2-oxoborn-3-ylidene) methyl]benzyl]acrylamide;
1,4-bisbenzimidazolylphenylene-3,3',5,5'-tetrasulfonic acid and its soluble salts;
polyorganosiloxanes containing a benzalmalonate function;
polyorganosiloxanes containing a benzotriazole function such as Drometrizole Trisiloxane.

The compositions according to the invention may also contain agents for tanning and/or for artificial tanning of the skin (self-tanning agents), such as, for example, dihydroxyacetone (DHA).

The cosmetic compositions according to the invention may also contain pigments or, alternatively, nanopigments (mean size of the primary particles: generally ranging from 5 nm to 100 nm, preferably from 10 nm to 50 nm) of metal oxides, coated or uncoated, such as, for example, nanopigments of titanium dioxide (amorphous or crystallized in the rutile and/or anatase state), of iron oxide, zinc oxide, zirconium oxide or cerium oxide, which are all UV photoprotective agents well known per se. Conventional coating agents are moreover alumina and/or aluminum stearate. Such nanopigments of metal oxides, coated or uncoated, are, in particular, described in EP-A-0,518,772 and EP-A-0,518,773.

The compositions of the invention may comprise, in addition, conventional cosmetic additives and adjuvants selected, in particular, from among fatty substances, organic solvents, thickeners, demulcents, opacifiers, colorants, stabilizers, emollients, antifoaming agents, moisturizing agents, perfumes, preservatives, polymers, fillers, sequestrants, propellants, alkalinizing or acidifying agents or any other ingredient customarily formulated into cosmetics, in particular for the production of anti-sun/sunscreen compositions in the form of emulsions.

The fatty substances may be an oil or a wax or mixtures thereof, and they also comprise fatty acids, fatty alcohols and esters of fatty acids. The oils may be selected from among animal, vegetable, mineral or synthetic oils and, in particular, from among liquid paraffin, paraffin oil, silicone oils, volatile or otherwise, isoparaffins, polyolefins, fluorinated or perfluorinated oils. Likewise, the waxes may be animal, fossil, vegetable, mineral or synthetic waxes which are also known per se.

Exemplary organic solvents include the lower alcohols and polyols.

Of course, one skilled in this art will take care to select this or these optional additional compounds and/or their quantities such that the advantageous properties, in particular the resistance to water, the stability, which are intrinsically associated with the emulsions in accordance with the invention are not, or not substantially, altered by the addition (s) envisaged.

The compositions of the invention may be formulated according to techniques well known to this art, in particular those suited for the preparation of emulsions of the oil-in-water or water-in-oil type.

The subject compositions may be provided, in particular, in the form of a simple or complex (O/W, W/O, O/W/O or W/O/W) emulsion such as a cream, a milk, a gel or a gel cream, of a powder, a lotion, an ointment, a solid stick and may optionally be packaged as an aerosol and provided in the form of a foam, mousse or spray.

When an emulsion is provided, the aqueous phase thereof may comprise a nonionic vesicular dispersion prepared according to known techniques (Bangham, Standish and Watkins, *J. Mol. Biol*, 13, 238 (1965), FR-2,315,991 and FR-2,416,008).

The cosmetic compositions according to the invention may be formulated for protecting the human epidermis or the hair against the damaging effects of ultraviolet radiation, as an anti-sun composition or as a makeup product.

When the cosmetic compositions according to the invention are formulated for protecting the human epidermis against UV rays, or as anti-sun/sunscreen compositions, same may be provided in the form of a suspension or a dispersion in solvents or fatty substances, in the form of a nonionic vesicular dispersion or, alternatively, in the form of an emulsion, preferably of the oil-in-water type, such as a cream or a milk, in the form of an ointment, a gel, a gel cream, a solid stick, a powder, a stick, an aerosol foam or a spray.

When the cosmetic compositions according to the invention are formulated for protecting the hair against UV rays, same may be provided in the form of a shampoo, a lotion, a gel, an emulsion, a nonionic vesicular dispersion and may constitute, for example, a rinse-off composition to be applied before or after shampooing, before or after dyeing or bleaching, before, during or after permanent-waving or hair straightening, a hair-styling or treatment lotion or gel, a lotion or gel for blow drying or hair setting, a composition for permanent waving or straightening, dyeing or bleaching the hair.

When the subject compositions are formulated as makeup products for the eyelashes, the eyebrows or the skin, such as a treatment cream for the epidermis, foundation, lipstick, eyeshadow, blusher, mascara or eyeliner, same may be provided in a solid or pasty, anhydrous or aqueous form, such as oil-in-water or water-in-oil emulsions, nonionic vesicular dispersions or alternatively suspensions.

For example, for the anti-sun formulations in accordance with the invention which have a carrier, vehicle or diluent of the oil-in-water emulsion type, the aqueous phase (comprising in particular the hydrophilic screening agents), generally constitutes from 50% to 95% by weight, preferably from 70% to 90% by weight, relative to the total weight of the formulation, the oily phase (comprising in particular the lipophilic screening agents), from 5% to 50% by weight, preferably from 10% to 30% by weight, relative to the total weight of the formulation, and the (co)emulsifier(s) from 0.5% to 20% by weight, preferably from 2% to 10% by weight, also relative to the total weight of the formulation.

As indicated above, the present invention thus features formulating the subject emulsions for the production of cosmetic compositions for protecting the skin and/or the hair against ultraviolet radiation, in particular solar radiation.

In order to further illustrate the present invention and the advantages thereof, the following specific examples of formulations A, B, C and D are given, it being understood that same are intended only as illustrative and in nowise limitative.

In said examples to follow, all parts are given by weight % with respect to the total weight of the composition.

EXAMPLES

| COMMON VEHICLE | % by weight |
|---|---|
| 80/20 Mixture of cetylstearyl alcohol and of oxyethylenated (33 EO) cetylstearyl alcohol (Sinnowax AO-Henkel) | 7 |
| Mixture of glycerol mono- and distearate (Cerasynt SD-V ISP) | 2 |
| Cetyl alcohol | 1.6 |
| Polydimethylsiloxane (Dow Corning 200 Fluid-Dow Corning) | 1.6 |
| Benzoate $C_{12}/C_{15}$ alcohols (Witconol TN-Witco) | 16 |
| 4-tert-Butyl-4'-methoxydibenzoylmethane, marketed under the trademark Parsol 1789 | X% AM |
| Glycerol | 16 |
| 2,2'-Methylenebis[6-(2H-benzotriazol-2-yl)4-(1,1,3,3-tetramethylbutyl)phenol] in the micronized form, marketed under the trademark Tinosorb M by Ciba-Geigy Mean particle size 0.15–0.2 µm | Y% AM |
| Preservatives | q.s. |
| EDTA | 0.1 |
| Demineralized water, q.s. for | 100 |

| Composition Examples | 2,2'-Methylenebis[6-(2H-benzotriazol-2-yl)-4-(1,1,3,3-tetramethylbutyl)phenol] in the micronized form Y% | 4-tert-Butyl-4'-methoxydibenzoyl-methane X% |
|---|---|---|
| A | 1.0 | 0.5 |
| B | 10.0 | 0.5 |
| C | 10.0 | 2.0 |
| D | 1.0 | 2.0 |

For each of these compositions, the percentage of residual 4-tert-butyl-4'-methoxydibenzoylmethane and the percentage of residual 2,2'-methylenebis[6-(2H-benzotriazol-2-yl)-

4-(1,1,3,3-tetramethylbutyl)phenol] after irradiation with UV-radiation were determined according to the following protocol:

3 test samples and 3 control samples were prepared for each formula. 2 mg/cm² of formula were deposited with a spatula on poly(methyl methacrylate) plaques. The test plaques were exposed for 1 h, 39 min, to a Suntest Heraeus equipped with a Xenon lamp having, as UV-A flux, $3.02 \times 10^{-3}$ W/cm² and, as UV-B flux, $2.05 \times 10^{-4}$ W/cm², and the control plaques were stored for the same time and at the same temperature (35°–40°C.) in darkness. At the end of this time, the screening agents were extracted by immersing each plaque in 50 g of tetrahydrofuran and by subjecting them to ultrasound for 15 min in order to ensure good extraction. The solutions obtained were analyzed by high performance liquid chromatography. For each formula tested, the level of residual dibenzoylmethane after exposure is given by the ratio of its concentration in the exposed sample to its concentration in the unexposed sample. The results obtained are reported in the table below:

TABLE

| | Irradiation 1 hour solar UV-A Residual fraction | |
|---|---|---|
| Composition UV screening agent | 2,2'-Methylenebis-[6-(2H-benzotriazol-2-yl)-4-(1,1,3,3-tetramethylbutyl)-phenol] in the micronized form | 4-tert-Butyl-4'-methoxydibenzoyl-methane |
| A | (102 ± 2)% | (53 ± 2)% |
| B | (100 ± 2)% | (70 ± 2)% |
| C | (99 ± 3)% | (50 ± 3)% |
| D | (98 ± 1)% | (41 ± 4)% |

It was observed that the insoluble organic UV-screening agent conspicuously enhanced the photostability of the dibenzoylmethane derivative with respect to UV-radiation.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for enhancing the UV-stability of at least one UV-photoprotecting dibenzoylmethane compound, comprising formulating therewith an effective UV-photostabilizing amount of at least one micronized insoluble organic UV-screening agent, the mean particle size of said micronized particles ranging from 0.01 to 2 μm.

2. The process as defined by claim 1, the mean particle size of said micronized particles ranging from 0.02 to 1.5 μm.

3. The process as defined by claim 2, the mean particle size of said micronized particles ranging from 0.03 to 1.0 μm.

4. The process as defined by claim 1, said micronized particles having been formed by grinding course particulates of said insoluble organic UV-screening agent in the presence of a surfactant.

5. The process as defined by claim 4, said surfactant comprising an alkyl polyglucoside having the formula $C_nH_{2n+1}O(C_6H_{10}O_5)_xH$ in which n is an integer ranging from 8 to 16 and x is the average degree of polymerization of the structural unit $(C_6H_{10}O_5)$ and varies from 1.4 to 1.6.

6. The process as defined by claim 4, said surfactant being present at a concentration ranging from 1% to 50% by weight relative to the insoluble organic UV-screening agent in its micronized state.

7. The process as defined by claim 1, said at least one UV-photoprotecting dibenzoylmethane compound being selected from the group consisting of:

2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

8. The process as defined by claim 7, said at least one UV-photoprotecting dibenzoylmethane compound comprising 4-(tert-butyl)-4'methoxydibenzoylmethane.

9. The process as defined by claim 7, said at least one UV-photoprotecting dibenzoylmethane compound comprising 4-isopropyldibenzoylmethane.

10. The process as defined by claim 1, said at least one insoluble organic UV-screening agent comprising an oxanilide, triazine, triazole, vinylamide, or cinnamide.

11. The process as defined by claim 10, said at least one insoluble organic UV-screening agent comprising an oxanilide having the structural formula (1):

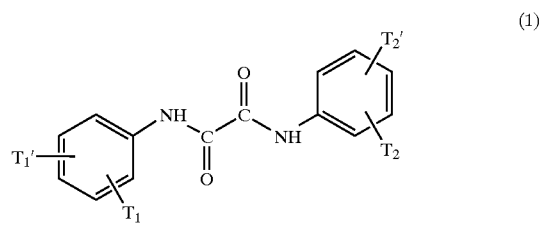

in which $T_1$, $T'_1$, $T_2$ and $T'_2$, which may be identical or different, are each a $C_1$–$C_8$ alkyl radical or a $C_1$–$C_8$ alkoxy radical.

12. The process as defined by claim 10, said at least one organic UV-screening agent comprising an insoluble s-triazine bearing benzalmalonate and/or phenylcyanoacrylate substituents.

13. The process as defined by claim 12, said at least one triazine UV-screening agent comprising 2,4,6-tris(diethyl 4'-aminobenzalmalonate)-s-triazine; 2,4,6-tris(diisopropyl 4'-aminobenzalmalonate)-s-triazine; 2,4,6-tris(dimethyl 4'-aminobenzalmalonate)-s-triazine or 2,4,6-tris(ethyl α-cyano-4-aminocinnamate)-s-triazine.

14. The process as defined by claim 10, said at least one insoluble organic UV-screening agent comprising a triazine having the following structural formula:

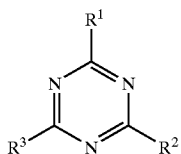

(2)

in which $R^1$, $R^2$, $R^3$ are independently phenyl, phenoxy, or pyrrolo radicals, optionally substituted with one, two or three substituents selected from among OH, $C_1$–$C_{18}$ alkyl or alkoxy, $C_1$–$C_{18}$ carboxyalkyl, $C_5$–$C_8$ cycloalkyl, a methylidenecamphor group, a radical —(CH=CH)$_n$(CO)—OR$^4$, wherein $R^4$ is $C_1$–$C_{18}$ alkyl or cinnamyl, and n is equal to 0 or 1.

15. The process as defined by claim 10, said at least one organic UV-screening agent comprising an s-triazine bearing benzotriazole and/or benzothiazole substituents.

16. The process as defined by claim 15, said at least one insoluble triazine UV-screening agent comprising 2,4,6-tris[(3'-benzotriazol-2-yl-2'-hydroxy-5'-methyl)phenylamino]-s-triazine, or 2,4,6-tris[(3'-benzotriazol-2-yl-2'-hydroxy-5'-ter-octyl)phenylamino]-s-triazine.

17. The process as defined by claim 10, said at least one insoluble organic UV-screening agent comprising a triazole having the following structural formula (3):

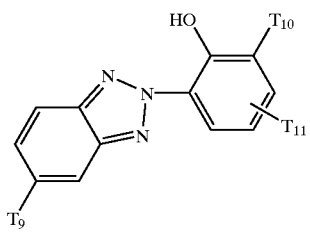

(3)

in which $T_9$ is a hydrogen atom or a $C_1$–$C_{18}$ alkyl radical; and $T_{10}$ and $T_{11}$, which may be identical or different, are each a $C_1$–$C_{18}$ alkyl radical which is optionally substituted with a phenyl radical.

18. The process as defined by claim 17, said compound of formula (3) being selected from among:

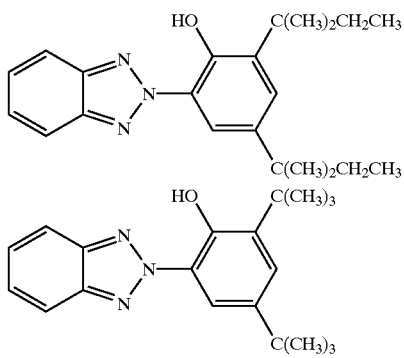

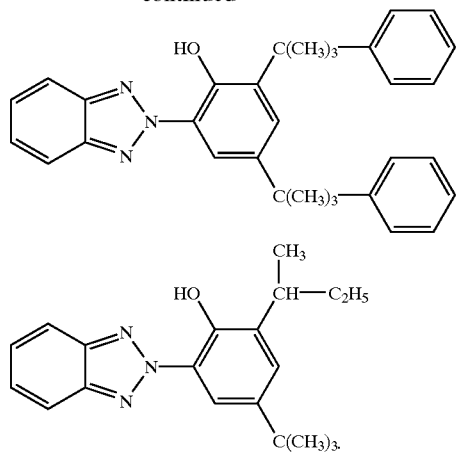

19. The process as defined by claim 10, said at least one insoluble organic UV-screening agent comprising [2,4'-dihydroxy-3-(2H-benzotriazol-2-yl)-5-(1,1,3,3-tetramethylbutyl)-2'-n-octoxy-5'-benzoyl]diphenylmethane having the structural formula:

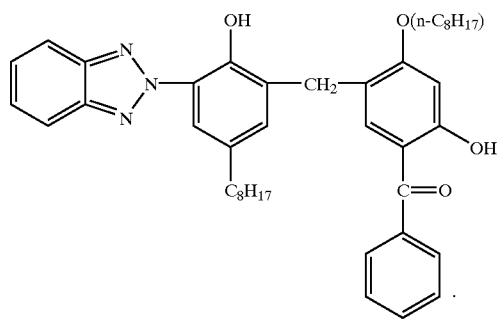

20. The process as defined by claim 10, said at least one insoluble organic UV-screening agent comprising a methylenebis(hydroxyphenylbenzo-triazole) having the following structural formula:

(4)

in which the radicals $T_{12}$ and $T_{13}$, which may be identical or different, are each a $C_1$–$C_{18}$ alkyl radical optionally substituted with one or more $C_1$–$C_4$ alkyl, $C_5$–$C_{12}$ cycloalkyl, or aryl radicals.

21. The process as defined by claim 20, said compound of formula (4) being selected from among:

compound (a)

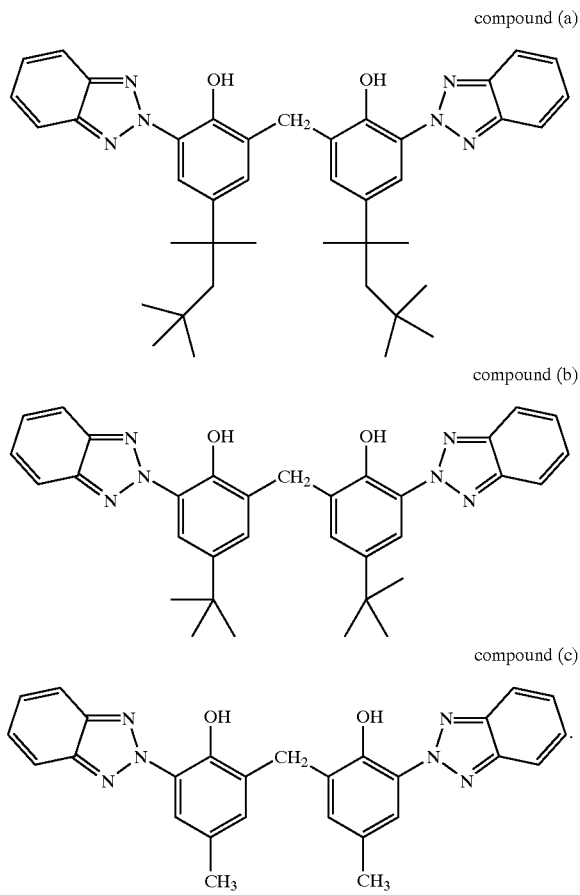

compound (b)

compound (c)

22. The process as defined by claim 10, said at least one insoluble organic UV-screening agent comprising a vinylamide having the following structural formula:

$$T_{14}-(Y)r-C(=O)-C(T_{15})=C(T_{16})-N(T_{17})(T_{18}) \quad (5)$$

in which $T_{14}$ is a $C_1$–$C_{18}$ alkyl radical or a phenyl radical which is optionally substituted with one, two or three radicals selected from among OH, $C_1$–$C_{18}$ alkyl, $C_1$–$C_8$ alkoxy, or a radical —C(=O)—O$T_{19}$ wherein $T_{19}$ is a $C_1$–$C_{18}$ alkyl radical; $T_{15}$, $T_{16}$, $T_{17}$ and $T_{18}$, which may be identical or different, are each a $C_1$–$C_{18}$ alkyl radical or a hydrogen atom; Y is N or O and r is equal to 0 or 1.

23. The process as defined by claim 22, said compound of formula (5) comprising 4-octylamino-3-penten-2-one; ethyl 3-octylamino-2-butenoate; 3-octylamino-1-phenyl-2-buten-1-one; or 3-dodecylamino-1-phenyl-2-buten-1-one.

24. The process as defined by claim 10, said at least one insoluble organic UV-screening agent comprising a cinnamamide having the following structural formula:

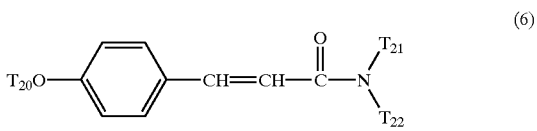

(6)

in which OT$_{20}$ is a hydroxyl or $C_1$–$C_4$ alkoxy radical; $T_{21}$ is hydrogen or $C_1$–$C_4$ alkyl; $T_{22}$ is a radical —(CONH)s-phenyl wherein s is equal to 0 or 1 and the phenyl group may be substituted with one, two or three groups selected from among OH, $C_1$–$C_{18}$ alkyl, $C_1$–$C_8$ alkoxy, or a radical —C(=O)—OT$_{23}$ wherein $T_{23}$ is a $C_1$–$C_{18}$ alkyl, phenyl, 4-methoxyphenyl or phenylaminocarbonyl group.

25. The process as defined by claim 10, said at least one insoluble organic UV-screening agent comprising a cinnamamide dimer.

26. The process as defined by claim 25, said insoluble organic UV-screening agent having the structural formula:

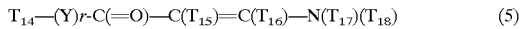

27. The process as defined by claim 1, said at least one insoluble organic UV-screening agent comprising a polyvalent metal salt of a sulfonic or carboxylic organic screening agent.

28. The process as defined by claim 27, said at least one insoluble organic UV-screening agent comprising a polyvalent metal salt of a sulfonated derivative of benzylidenecamphor, a polyvalent metal salt of a sulfonated derivative of benzimidazole, or a polyvalent metal salt of a derivative of cinnamic acid.

29. The process as defined by claim 1, said at least one insoluble organic UV-screening agent comprising a complex of a polyvalent metal or of ammonium with organic UV-A and/or UV-B screening agents.

30. A topically applicable, UV-photostable and UV-photoprotecting cosmetic/dermatological composition, comprising at least one UV-photoprotecting dibenzoylmethane compound and an effective UV-photostabilizing amount therefor, of at least one micronized insoluble organic UV-screening agent, the mean particle size of said micronized particles ranging from 0.01 to 2 μm.

31. The UV-photostable and UV-photoprotecting cosmetic/dermatological composition as defined by claim 3, formulated into a topically applicable, cosmetically/dermatologically acceptable vehicle, diluent or carrier therefor.

* * * * *